United States Patent [19]

Wright

[11] Patent Number: 5,216,638
[45] Date of Patent: Jun. 1, 1993

[54] METHOD AND APPARATUS FOR THE ACOUSTIC INVESTIGATION OF A CASING CEMENTED IN A BOREHOLE

[75] Inventor: Peter Wright, Dallas, Tex.

[73] Assignee: Schlumberger Technology Corporation, New York, N.Y.

[21] Appl. No.: 513,243

[22] Filed: Apr. 20, 1990

[30] Foreign Application Priority Data

Apr. 26, 1989 [FR] France ................... 89 05520

[51] Int. Cl.⁵ .................. G01V 1/40; G01N 29/04
[52] U.S. Cl. ......................... 367/35; 367/30; 367/47; 73/579; 73/630; 364/422; 364/582
[58] Field of Search ............. 367/35, 29, 30, 47, 367/86; 73/579, 630; 364/422, 582; 181/105

[56] References Cited

U.S. PATENT DOCUMENTS

| | | | |
|---|---|---|---|
| 3,697,937 | 10/1972 | Ingram | 367/29 |
| 4,131,875 | 12/1978 | Ingram | 367/35 |
| 4,218,766 | 8/1980 | Parrack et al. | 367/47 |
| 4,255,798 | 3/1981 | Havira | 181/105 |
| 4,685,092 | 8/1987 | Dumont | 367/35 |
| 4,703,427 | 10/1987 | Catala et al. | 364/422 |
| 4,928,269 | 5/1990 | Kimball et al. | |

FOREIGN PATENT DOCUMENTS

2491123 4/1982 France.

OTHER PUBLICATIONS

Roberts et al; "Cement and Casing Evaluation Using Sonic and Ultrasonic Techniques"; 32nd Annu. SW Pert. Short Course Ass. et al Mtg, Lubbock Texas, Apr. 23, 1985, pp. 67-95, abst. only provided.

Hsu, K; "Wave Separation . . . Transformation"; Geophysics, vol. 55, #2, pp. 176-184, Feb. 1990, abst. only.

Kimball, C. V., "Improved Processing for Cement Evaluation" (oil industry application), presented at the Third Course of the International School on Physical Acoustics, Erice, Italy, Oct. 20-30, 1988.

U.S. application Ser. No. 494,721 Huau.

R. Kuc, "Bounds on estimating the acoustic attenuation of small tissue regions from reflected ultrasound," Proceedings of the IEEE, vol. 73, No. 7, Jul. 1985, pp. 1159-1168.

*Primary Examiner*—Nelson Moskowitz
*Attorney, Agent, or Firm*—Marc D. Foodman

[57] ABSTRACT

Method for determining at least one characteristic of a casing cemented in a borehole, such as cement bond and casing thickness, from a reflected acoustic signal S(t) obtained by directing an acoustic pulse at a substantially normal incidence towards a radial sector of the wall of the casing, the pulse stimulating thickness resonance within the walls of the casing. The method according to the invention comprises the steps of: determining a first time window corresponding to a first portion of signal S(t) including the initial reflection from the casing and subsequent acoustic returns due to resonance, determining a second time window corresponding to a second portion of signal S(t) mainly including the initial reflection from the casing, and determining the casing characteristic from information related to resonance contained in the first time window while normalizing the information by information contained within the second time window.

15 Claims, 6 Drawing Sheets

METHOD AND APPARATUS FOR THE ACOUSTIC INVESTIGATION OF A CASING CEMENTED IN A BOREHOLE

BACKGROUND OF THE INVENTION

1. Technical Field

The present invention is directed to acoustic inspection of a casing cemented in a borehole. More particularly, the present invention is directed to acoustic inspection of the casing for determining specific properties relating to the casing and the surrounding materials, while simultaneously compensating for variations in the acoustic pulse and acoustic attenuation caused by mud filling the borehole.

2. Background Information

In general, once a well has reached a desired depth, the borehole is cased with cement being injected into the annular space between the casing and the wall of the borehole to prevent fluid communication between various geological strata. In order to determine whether such unwanted communication nevertheless exists, measurements may be performed downhole by means of a logging tool. These measurements determine the quality of the bond between the cement and the casing. Additionally, casing thickness can be derived from these measurements.

It has long been the practice to use acoustic waves for performing such measurements. Such techniques have relied on measurements which are averages in the circumferential and/or longitudinal direction of the casing, and consequently cannot identify localized phenomena such as longitudinal hydraulic communication paths. A complete presentation of prior art techniques can be found in U.S. Pat. No. 4,255,798 to Havira, assigned to the same assignees as the present invention and herein incorporated by reference.

Of the techniques that have sought to improve the vertical and radial resolution in such inspection, the technique described in the above-mentioned Havira patent turns out to have been an extremely important breakthrough. This technique consists of emitting an acoustic pulse over a radial sector of the casing, with the pulse being constituted by acoustic waves at frequencies selected to cause resonance to appear across the thickness of the casing; in determining the energy present in a reverberation segment of the reflected signal; and in characterizing from the energy the quality of the bond of the cement behind the radial sector of the casing. The reverberation segment under consideration is selected so as to be substantially representative of acoustic reverberation between the walls of the casing. Rapid damping of the resonance, i.e., low energy, indicates cement behind the casing, whereas slow damping, i.e., high energy, indicates an absence of cement.

A logging tool using the Havira technique is described in a commercial brochure entitled "Cement Evaluation Tool" published by Schlumberger in June 1983, incorporated herein by reference. The sonde, preferably centered within the casing, includes eight transducers distributed helically at 45° intervals, thereby obtaining good coverage around the periphery of the casing. Acoustic pulses are fired sequentially. They are likewise received sequentially, analyzed and transmitted to the surface where they are processed.

In addition, a ninth transducer, commonly referred to as the "reference" transducer, points along the axis of the casing towards a reflecting wall which is plane and disposed at a fixed distance from the reference transducer. The reflection signal detected by the ninth transducer is used to determine in situ the propagation time through the borehole fluid (mud), i.e. the time interval between emission and reception of the acoustic wave. The wave's propagation velocity through the mud is deduced therefrom. Given the propagation velocity of the wave, it is possible to determine the apparent radius of the casing for each of the eight transducers. It is particularly advantageous to obtain this radius since it makes it possible, in particular, to detect any possible deformation of the casing and to monitor the centering of the sonde inside the casing in order to obtain an indication of the validity and the quality of the measurements as performed.

In this technique, a portion of the reflected acoustic signal, representative of acoustic reflections between the walls of the casing, is analyzed. A signal $QC_i$ is derived therefrom, representative of the quality of the bond of the cement with the casing, on the basis of the energy W2 measured in a reverberation segment of the reflected signal S.

The changes in amplitude of signal S as a function of time, as received by a transducer, are shown in FIG. 2. The effects due to mud are taken into account by normalizing the measured energy W2 relative to the peak amplitude signal W1. Nevertheless, it turns out that normalization does not give complete satisfaction since quantitative interpretation of the measurements shows up problems of divergence in the measurements.

Tests and experiments performed by Applicant have shown that these differences to a large extent can be attributed to a large extent to the fact that the conventional processing is sensitive to the properties of the mud, to the characteristics of the transducer and of its drive electronics.

The Applicant has observed that the normalization of the portion of the signal at energy W2 was being performed using a peak amplitude signal W1 which did not correspond to the same frequencies as those present in the portion of the signal corresponding to the energy W2.

In general, the energy W1 is not at the same frequency as the energy W2, even in water. The energy W1 is a measure of the energy maximum conveyed by a spectrum component which depends on the properties of the pulse, i.e. the characteristics of the transducer and its drive electronics, and on the attenuation by the mud, whereas the energy W2 includes energy only around the resonance frequency of the casing.

SUMMARY OF THE INVENTION

The Applicant proposes a different concept for processing the reflected acoustic signal, whereby variations in acoustic pulse characteristics and mud attenuation can be compensated for in a satisfactory fashion and the reliability of the cement bond and other information obtained from the measurements can be improved.

There is provided according to the invention a method for determining at least one characteristic of a casing cemented in a borehole, such as cement bond or casing thickness, from a reflected acoustic signal S(t) obtained by directing an acoustic pulse at a substantially normal incidence towards a radial sector of the wall of the casing, said pulse stimulating thickness resonance within the walls of the casing, comprising the steps of defining a first time window corresponding to a first portion of signal S(t) including the initial reflection from the casing and subsequent acoustic returns due to resonance, defining a second time window corresponding to a second portion of signal S(t) mainly including the initial reflection from the casing, and determining the casing characteristic from information related to resonance contained in the first time window while normalizing the information by information contained within the second time window.

DESCRIPTION OF THE PREFERRED EMBODIMENT

Figure 1:
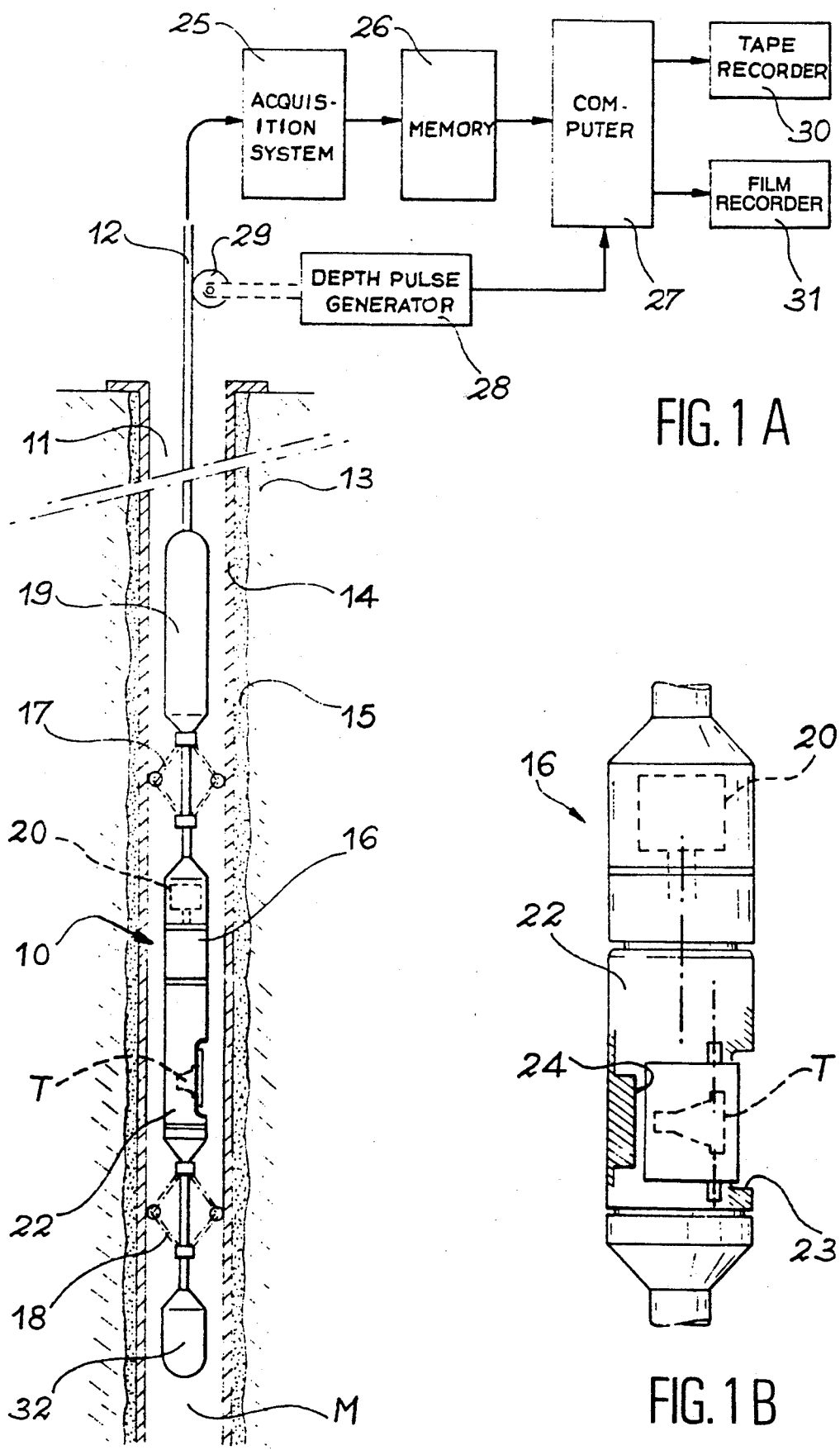
FIG. 1A is a diagram of an apparatus for cement evaluation, the apparatus being shown in use in a borehole.
FIG. 1B shows in more detail the sonde of the apparatus of FIG. 1A.

With reference to FIG. 1, an acoustic logging apparatus for studying the quality of the cement bond comprises downhole device 10 suspended in borehole 11 at the end of multiconductor cable 12.

The borehole, typically filled with a fluid such as drilling mud M, passes through strata 13 and is lined with casing 14. Cement 15 occupies the annular space between the casing and the geological strata traversed by the borehole. This logging apparatus is based on the measurement concept of casing resonance as disclosed in the above-mentioned Havira patent.

In general, downhole device 10 is an elongate body including sonde 16, top and bottom centralizers 17 and 18 for holding sonde 16 centered on the axis of casing 14, acoustic compensation section 22, hydraulic compensation section 32, and electronics section 19.

Various embodiments are possible for sonde 16. In a first embodiment, the sonde may comprise eight acoustic transducers angularly distributed around the sonde and disposed helically so as to enable eight sectors of casing to be inspected, as described in Havira or U.S. Pat. No. 4,685,092 to Dumont, assigned to the same assignee as the present invention and herein incorporated by reference.

In a second embodiment, described in U.S. application Ser. No. 494,721 filed Mar. 16, 1990 to Huau, assigned to the same assignee as the present invention and herein incorporated by reference, the sonde has a single acoustic transducer having a drive motor for rotating the assembly carrying the transducer about the axis of the sonde. Thus, the sonde can investigate the entire periphery of the borehole by continuously rotating the transducer.

In the preferred embodiment, as shown with reference to FIG. 1B, transducer T is rotatable about its offset drive shaft and an abutment to allow, in a calibration mode, transducer T to be rotated into a position where it looks at reflector 24.

Centralizers 17 and 18 are conventional and are provided with known means (not shown) for establishing electrical and/or hydraulic connections between the top portion and bottom portion of each of the centralizers.

Hydraulic compensation section 32 is conventional and serves to keep the pressure of the fluid in the hydraulic circuits at the same pressure as the borehole fluid M, i.e., the hydrostatic pressure of the well, thereby avoiding excessive differential pressures on sensitive portions of the sonde.

Acoustic compensation section 22, as shown in detail with reference to FIG. 1B, has hollow portion 23 open to the mud. Transducer T emits acoustic waves through the hollow portion along an axis which is substantially perpendicular to the axis of the sonde, either towards reflector 24 (in the calibration mode) or towards the casing (normal measurement mode). Reflector 24, substantially perpendicular to the emission axis of transducer T, simulates a radial sector of the casing under investigation.

Transducer T is preferably controlled to emit acoustic pulses of short duration and having a spectrum covering a frequency range from 200 kHz to 700 kHz, with the mean frequency being about 500 kHz.

Since the transducer emits radially, each emitted pulse is reflected by the various interfaces it encounters, e.g., casing 14 or reflector 24, thereby giving rise to an echo signal which is detected by the same transducer.

The detected signals are transmitted to electronics section 19 by well known means. In the preferred embodiments of the electronics section, the signals are sampled at a selected rate, digitized, multiplexed, and transmitted to the surface via a modem (not shown) connected to conductors in cable 12. Other techniques, including storing all data downhole, will be readily apparent to those skilled in the art.

On the surface, the conductors of cable 12 are connected to acquisition system 25 including a modem for decoding the transmitted information, and also including a demultiplexer. The signals are then stored in memory 26. The memory is connected to computer 27 suitable for performing a sequence of processing stages at each depth. These stages are explained in greater detail below.

Signals representative of the depth of device 10 are generated by a displacement detector comprising pulse generator 28 controlled by wheel 29 bearing tangentially against cable 12. Pulse generator 28 delivers a pulse each time cable 12 has moved through a unit length.

The processing performed by computer 27 provides a first set of output signals delivered to magnetic recorder 30 for storage in digital form on a magnetic tape. The magnetic recording comprises, in particular, the signals received by the transducer. Preferably, for each depth, the computer also provides a second set of output signals to optical recorder 31, providing a graphical recording on a film, e.g., of the type described in French patent 2 491 123, herein incorporated by reference.

Figure 2:
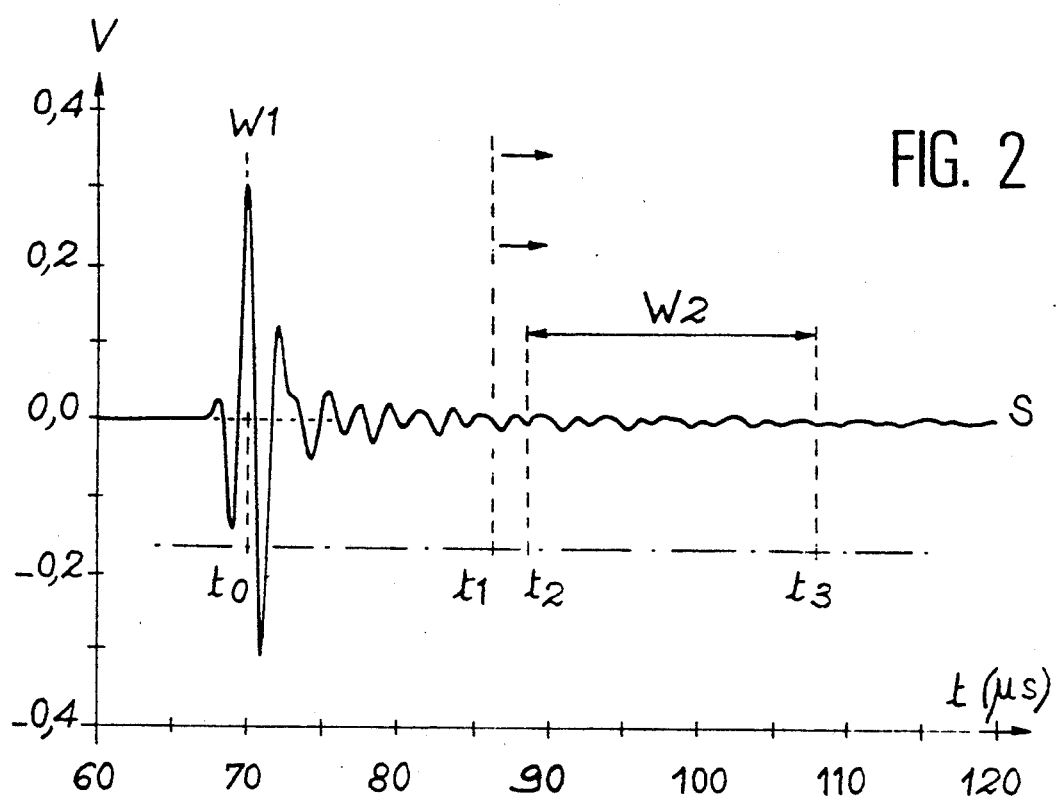
FIG. 2 shows a reflected acoustic signal S as detected by the transducer T, with signal portions W1, W2 as defined in the prior art method.

FIG. 2 shows the variations in the amplitude of a signal S as a function of time as detected by transducer T, and illustrates the method of windowing signal S disclosed in the Havira patent.

In Havira, a signal representative of the quality of the bond between the cement and the casing is produced from energy W2 measured in a portion of the reflected signal S which essentially correspond to reverberations between the walls of the casing as excited by the pulses emitted by the transducer. In window $t_2$-$t_3$, energy W2 may also include energy due to multiple reflections on the geological strata. These reflections can be observed from time $t_1$.

Energy W2 is normalized by maximum peak energy W1. This normalization serves to eliminate effects due to the mud, but it is not fully satisfactory as explained hereinabove.

Figure 3:
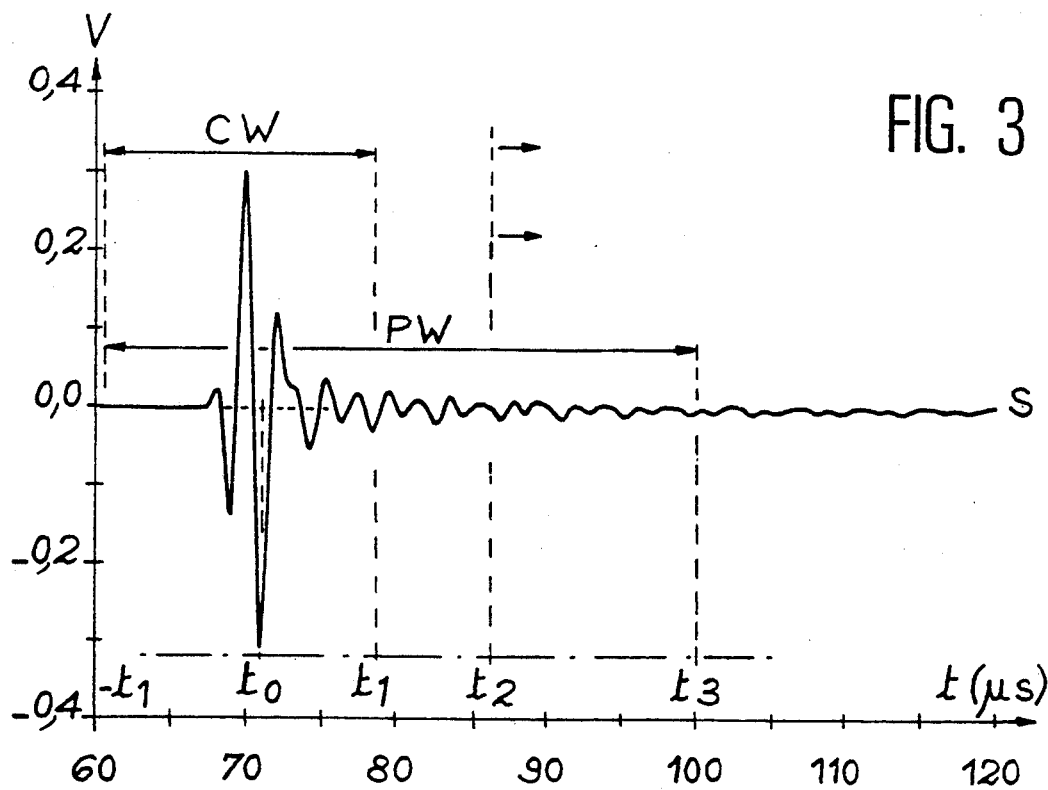
FIG. 3 shows a reflected acoustic signal S as detected by the transducer T, with signal portions CW and PW defined in accordance with the present invention.

FIG. 3 shows the same variations in amplitude of signal S as a function of time, together with two windows defined in detail below. Both windows include time reference or time origin $t_0$ located in the initial reflection portion of the signal.

Determining a Time Origin

According to the present invention, a stable time origin is determined in order to obviate the effects from noise and from variations in transducer response over different measurements. Several embodiments are possible.

In a first embodiment, analytic signal $S_a(t)$ is determined as follows:

$$S_a(t) = S(t) - iH(S(t))$$

where S(t) is the measured signal and H is the Hilbert transform of the measured signal, i being the square root of $-1$. The Hilbert transform can be obtained by any technique known in the art. Time origin $t_0$ is defined by the instant at which analytic signal $S_a(t)$ has a peak.

Another method of obtaining analytic signal $S_a(t)$ consists in performing a Fourier transform by any fast Fourier transform algorithm, then removing the negative frequencies by filtering, and subsequently performing a further fast Fourier transform on the signal obtained after filtering. The instant at which a peak occurs in the analytic signal is taken as being origin $t_0$.

An even faster method consists in rectifying the signal received by the transducer, extracting the amplitude maximum from the rectified signal, together with two extreme values on either side of the maximum to obtain three points defined by (time, amplitude) coordinates. A second order polynomial passing through these three points is then determined in conventional manner. The maximum of the resulting polynomial is determined and the time coordinate $t_0$ of the maximum is taken as being the time origin and serves as a reference for determining the position and duration of the windows.

Windowing the Signal S(t)

Portion PW of signal S(t) is defined by a wide time window ($-t_1$, $t_3$), referred to hereinafter as processing window. Portion PW obtained in this way includes the initial reflection of the acoustic signal from the inner wall of the casing and acoustic returns due to reverberations between the walls of the casing caused by its resonance in response to the acoustic pulse.

Portion CW of signal S(t) used for normalization purposes is defined by a narrow time window ($-t_1$, $+t_1$), referred to hereinafter as the normalization window, centered at time origin $t_0$ and can be defined as the early portion of the wide window. Portion CW thus defined mainly comprises the initial reflection from the wall of the casing.

Figure 4:
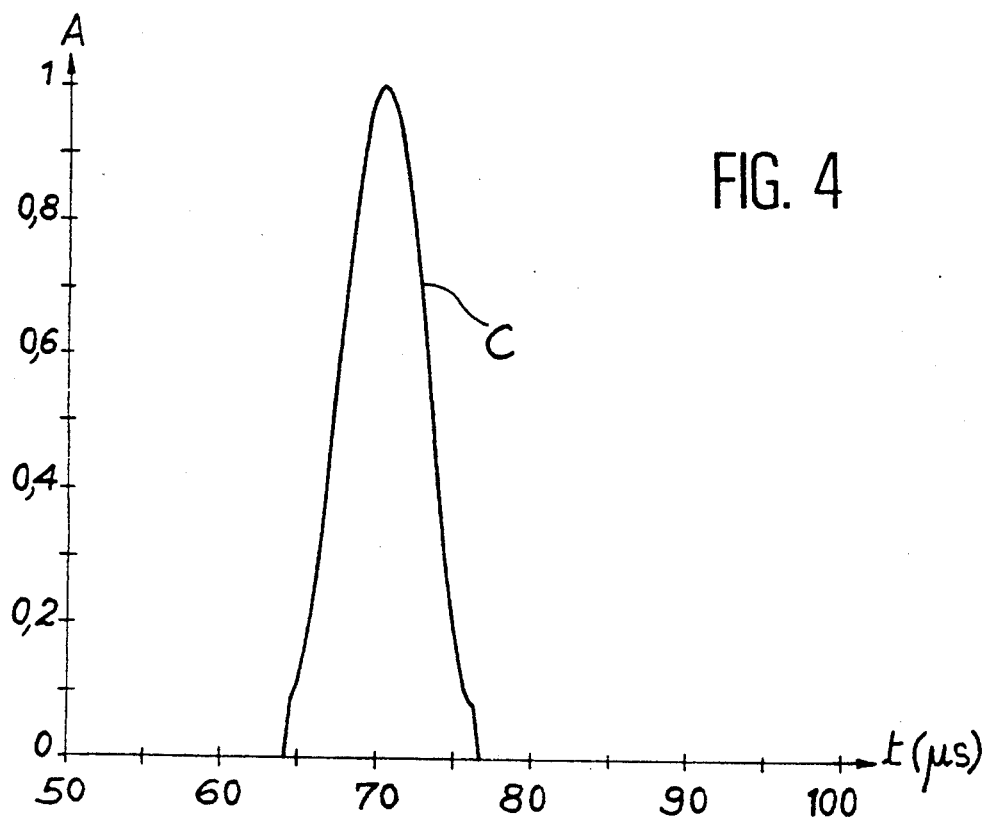
FIGS. 4 and 5 show the normalization window C and the processing window P, respectively, as defined in the method of the invention.
Figure 5:
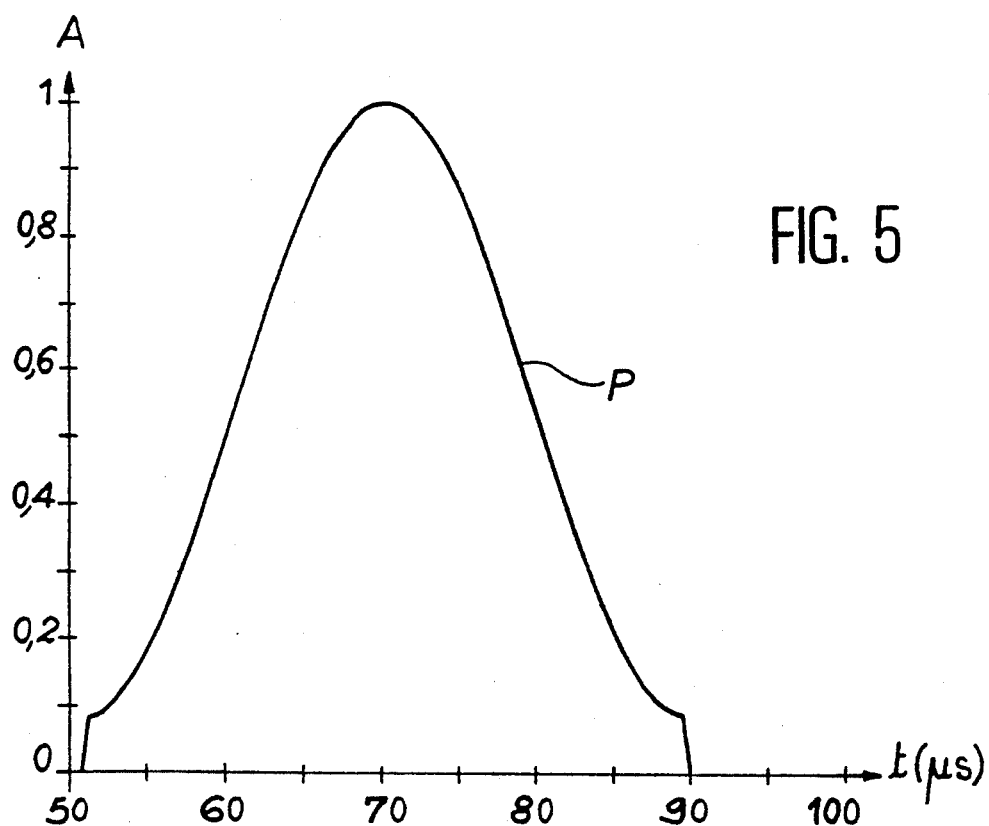

FIG. 4 shows an example of the windowing signal C(t) corresponding to a narrow window as used for normalization. FIG. 5 shows an example of the windowing signal P(t) corresponding to a wide window.

Windowed signals corresponding to CW and PW may be obtained by multiplying the signal S(t) by the signals shown in FIGS. 4 and 5, namely narrow window signal C(t) and wide window signal P(t).

The time intervals spanned by the windows are defined as multiples of the nominal resonance period of the casing, so as to automatically adapt the windows to the type (thickness) of casing under investigation.

Time intervals $-t_1, t_0$ and $t_0, t_1$ preferably lie in the range between 1.5 and 3 times the nominal resonance period of the casing, and are more preferably equal to 2.5 times this nominal period. Normalization window $-t_1, t_1$ thus lasts for a period preferably between 3 and 6 times the nominal resonance period of the casing, and more preferably a period equal to 5 times this nominal period.

A preferable range for time interval $t_0, t_3$ of the processing window is from 6 to 12 times, more preferably 6 to 8 times the nominal resonance period of the casing. Thus, the entire time interval $-t_1, t_3$ spanned by the processing window is preferably between 7.5 times and 15 times, more preferably between 7.5 and 11 times the nominal resonance period of the casing. As is well known to those skilled in the art, the nominal resonance period of the casing is determined from the nominal thickness of the casing and the sound velocity in the casing, both parameters being known.

For window signals C(t) and P(t), Hamming windows can be used. FIG. 4 shows such a Hamming window for C(t), centered on time origin $t_0$. As for processing window P(t), although FIG. 5 shows a symmetrical curve, it is preferred to use a Hamming window centered on the time origin $t_0$ but truncated at time $t_1$, i.e., an asymmetrical window signal.

Characterizing the Resonance of the Casing

The resonance of the casing in response to the acoustic pulse depends on the cement-casing bond, expressed as an acoustic impedance of the cement, and the casing thickness, which are the primary parameters of interest in the casing inspection. These parameters can be determined from a characterization of a resonance mode of the casing, e.g., the fundamental mode.

As noted above, wide processing window P(t) is preferably defined to contain the direct reflection from the casing and the early part of the resonance. Narrow window C(t) only contains the reflection from the casing and as such, windowed signal CW(t) provides information on the system formed by the pulse generating assembly—transducer and drive electronics—and the mud. In other words, it provides the response of the "infinite-block" (i.e., a casing of infinite thickness and extent). In the determination of the parameters of interest, the information contained in portion CW is used to normalize the information contained in signal S(t) within processing window P(t) to automatically compensate for variations (temperature, time, etc.) in the characteristics of the acoustic pulse and the attenuation of the mud.

Figure 6:
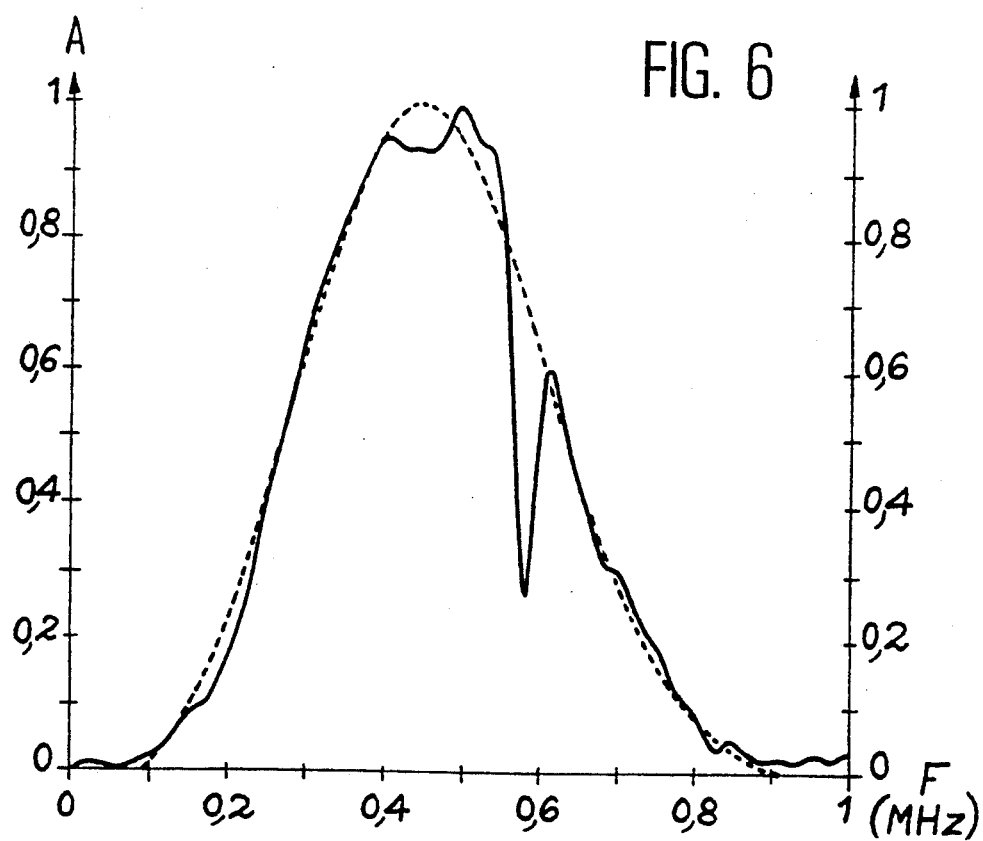
FIG. 6 shows the frequency spectrum of the signal amplitude, the solid line showing the signal windowed with the processing window and the dashed line showing the signal windowed with the normalization window.

To find and characterize the resonance, the frequency spectra of the windowed signals PW and CW are used. FIG. 6 shows the amplitude spectrum $PW(\omega)$ obtained from signal PW(t) (solid line), using a discrete Fourier transform, and the amplitude spectrum $CW(\omega)$ (dashed line) obtained likewise from signal CW(t). The resonance of the casing appears as a marked dip in signal $PW(\omega)$.

Figure 8:
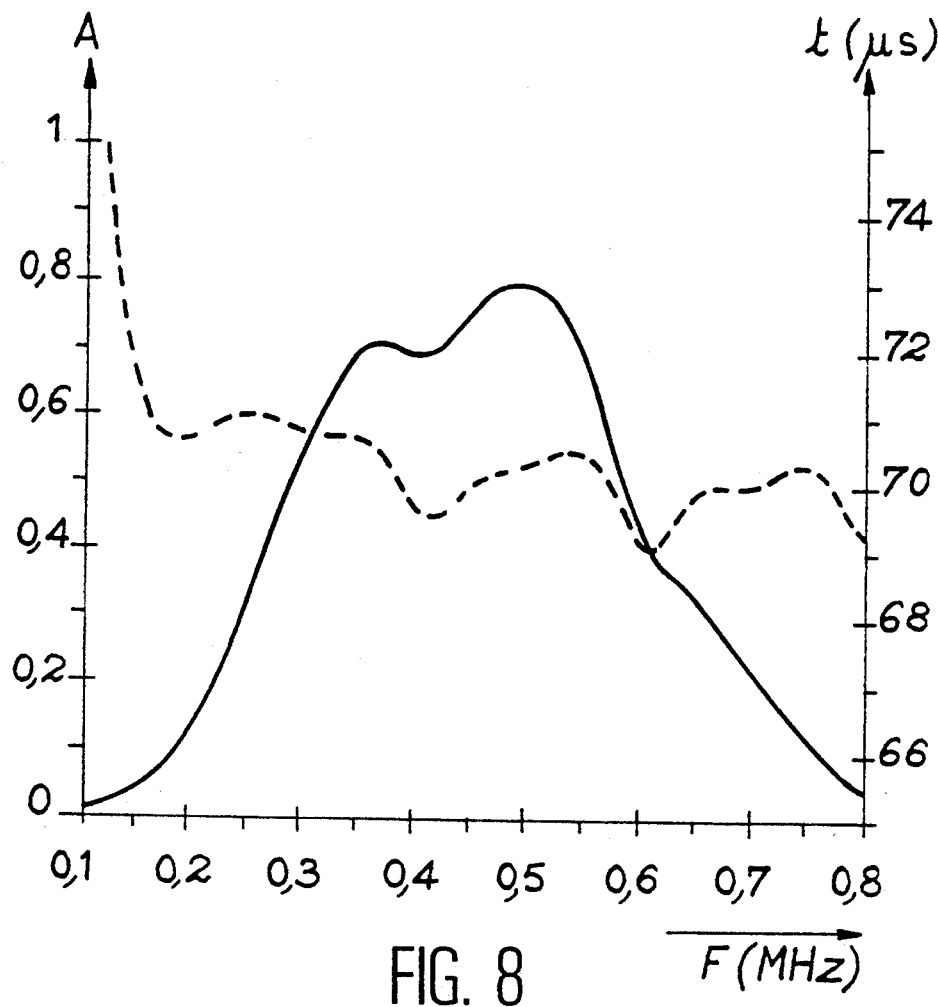
FIGS. 8 and 9 show the amplitude spectrum (solid line) and the group delay spectrum (dashed line) of the reflected signal as obtained from synthetic data for casings of two different thicknesses.
Figure 9:
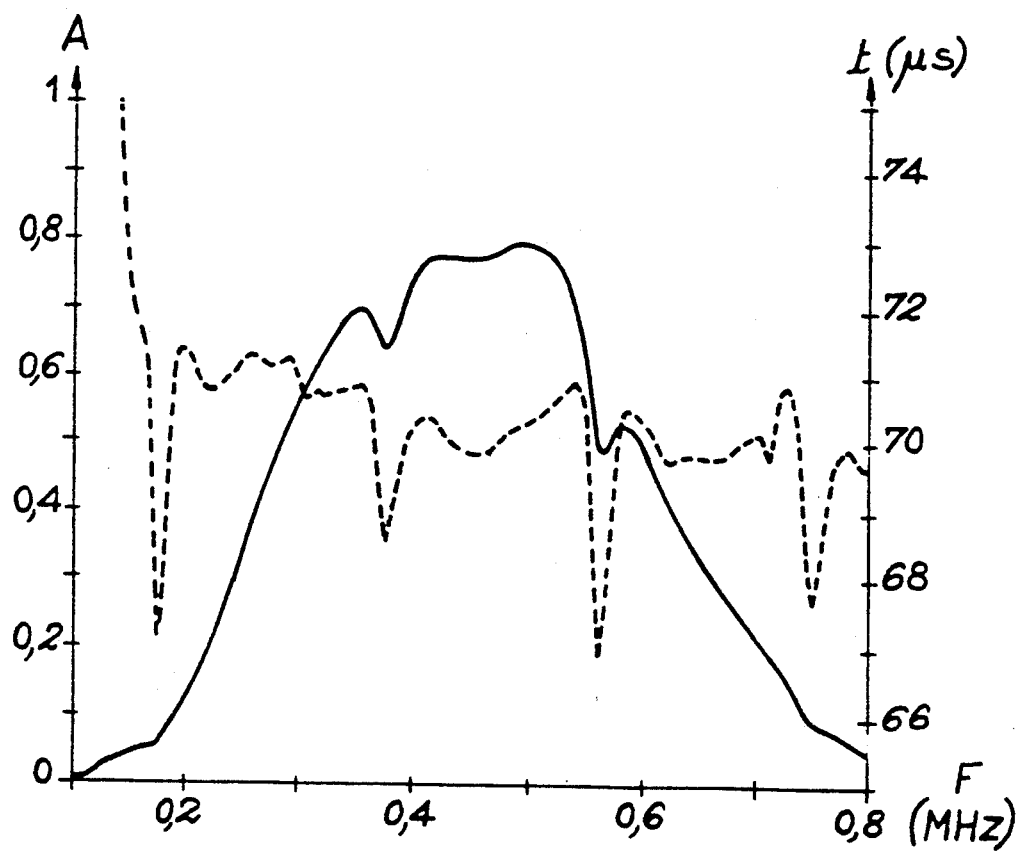

As the amplitude spectrum is highly dependent on transducer variations and attenuation by the borehole fluid, it is preferred to use the group delay spectrum. The group delay is defined as the derivative of radian phase versus angular frequency and is computed from the phase spectrum. The group delay response is advantageous as it tends to be smooth and linear except at resonances, thereby allowing easy identification and characterization of the resonance. This is illustrated in FIG. 8, which shows the theoretical amplitude (solid line) and group delay (dashed line) responses of a casing having a diameter of 178 millimeters (7 inches) and a thickness of 4 millimeters, in the case of a solid cement bond (cement impedance of 8 MRayl). FIG. 9 shows the amplitude and group delay responses of a casing of 178 millimeters diameter and 16 mm thickness, with the same cement bond.

Figure 7:
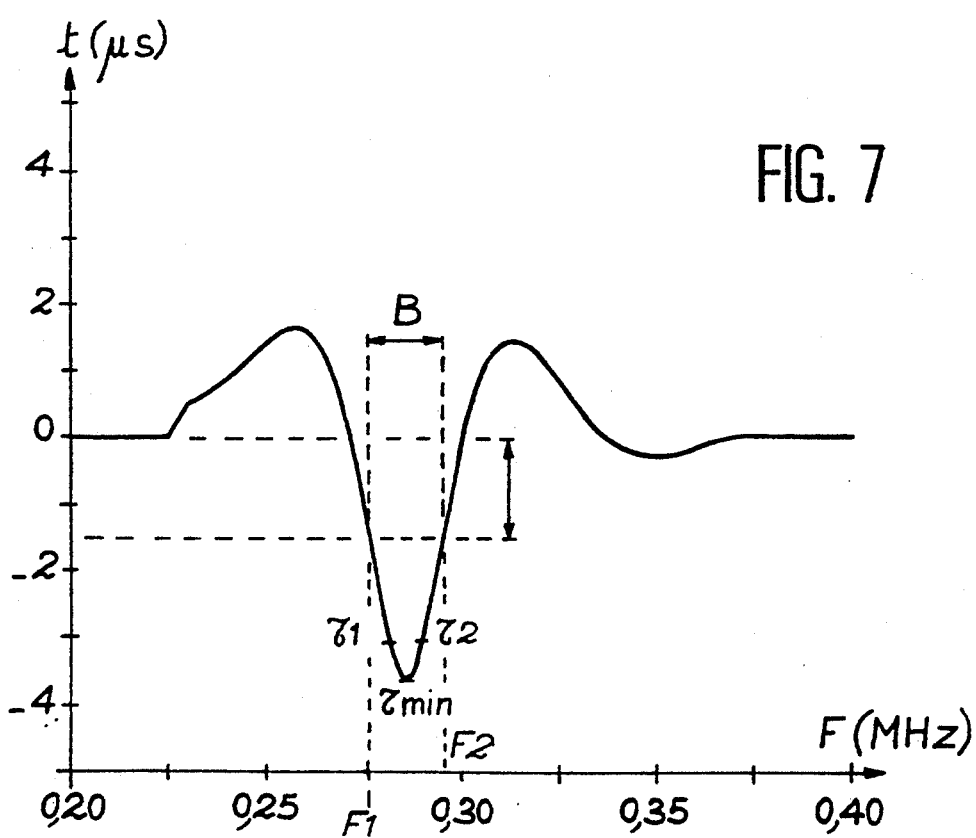
FIG. 7 shows a portion of the group delay spectrum of the signal after normalization, highlighting a dip indicative of a resonance.

FIG. 7 highlights the group delay spectrum around a resonance. The resonance can be characterized by central frequency $F_0$ of the resonance, corresponding to minimum group delay $\tau_{min}$, the depth H of the dip corresponding to the resonance, and the fractional bandwidth $B/F_0$. Bandwidth B is the width of the dip at a level $\Delta\tau$ above the group delay minimum $\tau_{min}$ equal to a predetermined percentage, e.g., 40%, of depth H of the dip: $B = F_2 - F_1$, with the corresponding group delays $\tau_2$ and $\tau_1$ such that $\tau_2 - \tau_{min} = \tau_1 - \tau_{min} = \Delta\tau = 0.4$ H. Central frequency $F_0$ is primarily dependent on the casing thickness while the depth and fractional bandwidth are primarily influenced by the acoustic impedances of the mud and the cement.

Determining Casing Thickness and Cement Impedance

A normalization step of the group delay spectrum is first performed in order to eliminate any slope, by linearizing the group delay spectrum of the normalization signal CW and subtracting it from the spectrum of the signal PW.

The parameters of the resonance are then determined, preferably by searching a minimum in the normalized group delay spectrum within a pre-determined frequency range located around the nominal resonance frequency of the casing. This yields values for the parameters $F_0$, H and $B/F_0$, which will be used as the "measured parameters" in the following description.

Figure 10:
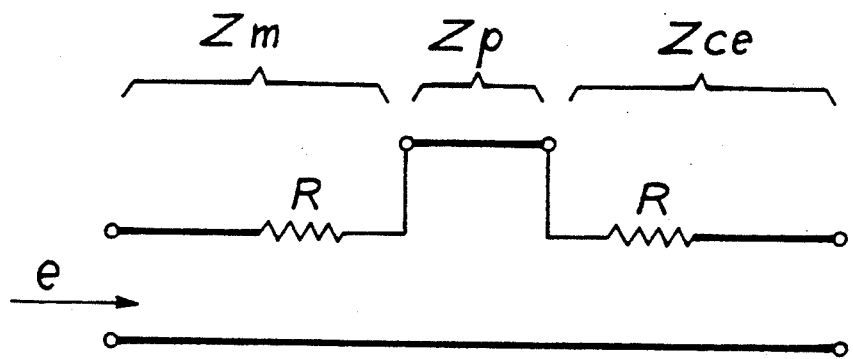
FIG. 10 is a diagram of an electromagnetic model of the casing, the cement and the mud, for use in a method for computing the cement impedance and thickness of the casing.

After the measured parameters of the resonance have been determined from the normalized group delay spectrum, the casing thickness and cement impedance are determined by iteration using a model, shown in FIG. 10. This model is a planar model (i.e., the casing wall is modelled as a plane) defined by cement impedance $Z_{ce}$, casing thickness d, mud impedance $Z_m$ and casing impedance $Z_p$. Mud impedance $Z_m$ is preferably obtained by separate calibration; casing impedance $Z_p$ is typically a known quantity. Resistances R can be added to the model to perform corrections taking into account the curvature of the casing, the resistances being set to values defined in accordance with the diameter of the casing.

The response of the model to a Dirac pulse e is determined in the frequency domain, with the initial value for the cement impedance $Z_{ce}$ obtained from the measured depth H of resonance by using look-up tables, and the initial value of casing thickness derived from central frequency $F_0$. This yields an impulse response spectrum of the model.

This spectrum is multiplied by the normalization spectrum $CW(\omega)$ representative of the transducer-mud system to obtain what can be termed the transducer-mud spectrum.

The processing window is applied in the frequency domain by convolution with the transducer-mud spectrum, and the group delay spectrum of the convoluted signal is computed.

The group delay spectrum is again normalized as described above by subtracting the linearized group delay spectrum of the normalization signal from the group delay spectrum of the convoluted signal.

The normalized group delay spectrum is used to determine "model" values for the parameters of the resonance, namely central frequency $F_{mod}$ corresponding to group delay minimum $\tau_{mid}$ identified in this spectrum within the specified frequency range, and fractional bandwidth $B_{mod}$ taken at a level $\tau_{mod} = \tau_{mid} + \Delta\tau$ ($\Delta\tau$ being as defined above). These model parameters are compared with the measured parameters. From the comparison, new estimates for the cement impedance and casing thickness are defined for a second iteration. The iteration is continued until the model group delay response is characterized by the same parameters as the measured resonance. Iteration may be performed by Newton-Raphson fitting technique, which typically requires only three iterations.

The planar model used in this method is quite simple and has the advantage of minimizing processing time.

A more exact model, based on the cylindrical geometry of the casing, could be used instead of the planar model. Such a cylindrical model would include additional parameters (e.g., casing diameter, transducer dimensions, transducer offset from the borehole axis, sound velocity in mud).

Alternative Computation Methods

Other computation methods can be envisioned with the same basic definitions of time windows C(t) and P(t) as specified above. An alternative method preferably consists of the following steps:

The entire signal S(t) is converted into the frequency domain before any windowing. Spectrum $S(\omega)$ thus obtained is normalized by spectrum $CW(\omega)$ derived from the calibration signal CW(t), the normalized amplitude being the ratio of the amplitudes and the normalized phase the difference between the phases.

The processing window is applied to the normalized spectrum in the frequency domain, by convolution of the normalized spectrum with the spectrum of the processing window.

The group delay spectrum is calculated from the result of the convolution. This allows the resonance to be characterized as described above, thus yielding central frequency, depth and fractional bandwidth.

From this point, it is possible to determine the cement impedance and casing thickness by direct computation, using pre-established look-up tables relating these parameters with the parameters which characterize the resonance. Another approach is to use the model as defined above. The computation steps will be as explained above, except that the step of normalizing the group delay spectrum can be dispensed with.

Although illustrative embodiments of the present invention have been described in detail with reference to the accompanying drawings, it is to be understood that the invention is not limited to those precise embodiments. Various changes or modifications may be effected therein by one skilled in the art without departing from the scope or spirit of the invention.

What I claim as my invention is:

1. A method for determining at least one characteristic of a casing cemented in a borehole, such as cement bond and casing thickness, from a reflected acoustic signal S(t) obtained by directing an acoustic pulse at a substantially normal incidence towards a radial sector of the wall of the casing, said pulse stimulating thickness resonance within the walls of the casing, comprising the steps of: determining a first time window corresponding to a first portion of signal S(t) including the initial reflection from the casing and subsequent acoustic returns due to resonance, determining a second time window corresponding to a second portion of signal S(t) mainly including the initial reflection from the casing, and determining said casing characteristic from information related to resonance contained in said first time window while normalizing said information by information contained within said second time window.

2. A method according to claim 1, wherein said second time window is defined so as to include the amplitude maximum of signal S(t).

3. A method according to claim 2, wherein the definition of the first and second time windows comprises the steps of determining the instant at which the amplitude maximum occurs in the signal, said instant being taken as a time origin $t_0$, and defining first and second time windows on the basis of this time origin.

4. A method according to claim 3, wherein, for determining the time origin, an analytic signal $S_a(t)$ of the response S(t) is determined; the amplitude maximum of the analytic signal is determined; and the time origin $t_0$ is determined as being that instant at which the amplitude maximum occurs in the analytic signal $S_a(t)$.

5. A method according to claim 4, wherein the analytic signal $S_a(t)$ is obtained by a Hilbert transform.

6. A method according to claim 4, wherein the analytic signal $S_a(t)$ is obtained by performing a Fourier transform, filtering to eliminate negative frequencies from the spectrum, and performing a further Fourier transform on the signal as obtained after filtering.

7. A method according to claim 3, wherein the time origin is defined by performing the following steps: extracting the absolute values of the amplitude maximum in the acoustic signal and of two extreme values situated on either side of said maximum; determining a second degree polynomial fitting these three values; and defining the time origin as the instant at which the polynomial is at a maximum.

8. A method according to claim 3, wherein the time intervals spanned by the time windows are defined by multiples of the nominal resonant period of the casing.

9. A method according to claim 8, wherein the second time window is centered on the time origin $t_0$, and extends on either side of the time origin over a period of time lying in the range from 1.5 and 3 times the nominal resonance period of the casing.

10. A method according to claim 8, wherein the first time window extends before the time origin $t_0$ over 1.5 to 3 times the nominal resonance period of the casing and after the time origin over 6 to 12 times said nominal resonance period.

11. A method according to claim 1, wherein said characteristic of the casing is determined by combining information derived from the frequency spectrum of the acoustic signal S(t) within the first time window and information derived from frequency spectrum of the acoustic signal S(t) within the second time window.

12. A method according to claim 11, comprising the step of determining the frequency spectra of the first portion of signal S(t) and of the second portion of signal S(t), respectively, normalizing the spectrum of the first portion by the spectrum of the second portion, and characterizing from said normalized spectrum the resonance of the casing, the parameters of the resonance being indicative of the characteristics of the casing.

13. A method according to claim 12, wherein the frequency spectra are the group delay frequency spectra.

14. A method for acoustic inspection of a casing cemented in a borehole, comprising the steps of obtaining a reflected acoustic signal S(t) by directing an acoustic pulse at a substantially normal incidence towards a radial sector of the wall of the casing, said pulse stimulating thickness resonance within the walls of the casing, defining a first time window corresponding to a first portion of signal S(t) including the initial reflection from the casing and subsequent acoustic returns due to resonance, defining a second time window corresponding to a second portion of signal S(t) mainly including the initial reflection from the casing, and determining at least one characteristic related to the casing from information related to resonance contained in said first time window while normalizing said information by information contained within said second time window.

15. An apparatus for acoustic inspection of a casing cemented in a borehole, comprising a sonde adapted for displacement in the borehole which includes transducer means for obtaining a reflected acoustic signal S(t) by directing an acoustic pulse at a substantially normal incidence towards a radial sector of the wall of the casing, said pulse stimulating thickness resonance within the walls of the casing; and signal processing means for performing the steps of defining a first time window corresponding to a first portion of signal S(t) including the initial reflection from the casing and subsequent acoustic returns due to resonance, defining a second time window corresponding to a second portion of signal S(t) mainly including the initial reflection from the casing, and determining at least one characteristic related to the casing from information related to resonance contained in said first time window while normalizing said information by information contained within said second time window.

* * * * *